(12) United States Patent
Ammerlaan (10) Patent No.: US 8,389,810 B2
(45) Date of Patent: Mar. 5, 2013

(54) LETTUCE VARIETY 41-49 RZ

(75) Inventor: Adrianus Martinus Jozeph Ammerlaan, Aramon (FR)

(73) Assignee: Rijk Zwaan Zaadteelt En Zaadhandel B.V., De Lier (NL)

( * ) Notice: Subject to any disclaimer, the term of this patent is extended or adjusted under 35 U.S.C. 154(b) by 140 days.

(21) Appl. No.: 12/697,378

(22) Filed: Feb. 1, 2010

(65) Prior Publication Data

US 2011/0191890 A1 Aug. 4, 2011

(51) Int. Cl.
*A01H 1/00* (2006.01)
*A01H 4/00* (2006.01)
*A01H 5/00* (2006.01)
*A01H 5/10* (2006.01)
*C12N 5/04* (2006.01)

(52) U.S. Cl. ........ 800/305; 800/260; 800/278; 800/298; 435/410; 435/430

(58) Field of Classification Search .................. None
See application file for complete search history.

(56) References Cited

U.S. PATENT DOCUMENTS 7,504,562 B2 * 3/2009 Schut et al. ............... 800/305
7,652,196 B2 * 1/2010 Ammerlaan ............... 800/305

* cited by examiner

*Primary Examiner* — Eileen B O Hara
(74) *Attorney, Agent, or Firm* — Vedder Price P.C.; Thomas J. Kowalski; Deborah L. Lu (57) ABSTRACT

The present invention relates to a *Lactuca sativa* L. var. longifolia Lam seed designated as 41-49 RZ, which has leaves with a hollow main vein, broad base leaves, and exhibits resistance against downy mildew (*Bremia lactucae* Regel), currant-lettuce aphid (*Nasonovia ribisnigri*), corky root (*Sphingomonas suberifaciens*) and lettuce mosaic virus (LMV). The present invention also relates to a *Lactuca sativa* L. var. longifolia Lam plant produced by growing the "41-49 RZ" seed. The invention further relates to methods for producing the lettuce cultivar, represented by lettuce variety 41-49 RZ.

26 Claims, 3 Drawing Sheets

LETTUCE VARIETY 41-49 RZ

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to a new lettuce (*Lactuca sativa*) variety which may be suitable for harvesting as hearts and wholeheads and resistant against *Nasonovia ribisnigri*.

BACKGROUND OF THE INVENTION

Romaine lettuce should provide a product at harvestable stage, which is acceptable to the processing industry and/or consumers. Therefore the harvestable product should not have tipburn, and it should have a dark green outer leaf color. Further it should be sufficiently headed, and as a result of this heading provide sufficient yellow-colored heartleaves.

Romaine lettuce is brought to the market in the form of wholehead, hearts, single leaves, or cut leaf pieces. For the purpose of wholehead and heart production it is very important that the leaves are wide enough to overlap and maintain head integrity. It also important that core internodes and petioles are short enough to give a closed base. The closed base and overlapping head leaves are reducing the product surface resulting in less wilting and a longer shelflife. This is desired by traders, retailers and consumers.

Lettuce can be attacked by many diseases and pests, such as downy mildew (*Bremia lactucae*), Lettuce Mosaic Virus (LMV), corky root (*Spingomonas suberifaciens*), and aphids. These problems have to be controlled by growers at high costs. Especially the currant-lettuce aphid *Nasonovia ribisnigri* is causing problems in lettuce, as it has the unique feature of multiplying deeply hidden in the heart of the lettuce plant. In the heart it cannot be reached by most insecticide treatments against aphids. Pesticides are used to control against these pests and diseases and they form a risk for the grower using them, as well as their residues are reducing the confidence of the potential consumers in the healthiness of the product.

Citation or identification of any document in this application is not an admission that such document is available as prior art to the present invention.

SUMMARY OF THE INVENTION

It is the object of the invention to provide a new type of romaine or cos lettuce, which is suitable for harvesting as hearts and wholeheads and does not have problems with aphids, downy mildew, corky root, and LMV. The harvested product is meant mainly for the wholeheads and hearts market.

The present invention fulfils this need by providing a new *Nasonovia*-resistant romaine or cos, lettuce (*Lactuca sativa* L. var. longifolia Lam) plant, which exhibits a combination of leaves with a hollow main vein, broad base leaves, LMV-resistance, corky root resistance and *Bremia*-resistance.

The present invention is further characterized by dark green outer leaves and resistance to *Nasonovia ribisnigri*.

The present invention provides seeds of the *Lactuca sativa* L. var. longifolia Lam plant designated as 41-49 RZ.

The present invention further provides pollen, ovules, and tissue cultures of regenerable cells from the plant produced by growing the seed of lettuce cultivar 41-49 RZ, in which the cells or protoplasts of the tissue that are cultured are produced from a tissue selected from leaves, pollen, embryos, cotyledons, hypocotyls, meristematic cells, roots, root tips, anthers, flowers, seeds or stems.

The present invention still further provides a lettuce plant regenerated from the above-described tissue cultures, in which the regenerated plant has all of the morphological and physiological characteristics of lettuce cultivar 41-49 RZ.

The present invention also relates to a transgenic version of the lettuce cultivar 41-49 RZ and to seed thereof.

The present invention further provides a method for producing a hybrid lettuce seed which may comprise crossing a first parent lettuce plant with a second parent lettuce plant and harvesting the resultant hybrid lettuce seed, wherein the first parent lettuce plant or the second parent lettuce plant is the lettuce plant produced by growing the seed of lettuce cultivar 41-49 RZ.

The present invention still further provides a method for developing a lettuce cultivar having leaves with a hollow main vein and broad base leaves which may comprise crossing a mother lettuce plant cultivar with a father lettuce plant cultivar to produce a hybrid seed; growing the hybrid seed to produce a hybrid plant; selfing the hybrid seed to produce F2 progeny seed; and selecting the F2 plants for having leaves with a hollow main vein and broad base leaves.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

DEPOSIT

The Deposits with National Collections of Industrial, Marine and Food Bacteria (NCIMB) in Bucksburn, Aberdeen AB21 9YA, Scotland, UK, under deposit accession number NCIMB Accession No. 41692 were made pursuant to the terms of the Budapest Treaty. Upon issuance of a patent, all restrictions upon the deposit will be removed, and the deposit is intended to meet the requirements of 37 CFR §§1.801-1.809. The deposit will be maintained in the depository for a period of 30 years, or 5 years after the last request, or for the effective life of the patent, whichever is longer, and will be replaced if necessary during that period.

DETAILED DESCRIPTION

The present invention provides *Lactuca sativa* L. var. longifolia Lam (romaine or cos lettuce) plant comprising leaves with a hollow main vein and broad base leaves, and resistance against the currant-lettuce aphid *Nasonovia ribisnigri*.

The present invention provides the *Lactuca sativa* L. var. longifolia Lam plant mentioned above with the following additional characteristics: dark green outer leaves, resistance against downy mildew *Bremia lactucae*, resistance against corky root *Sphingomonas suberifaciens*, and resistance against lettuce mosaic virus (LMV).

The present invention provides seeds of the *Lactuca sativa* L. var. longifolia Lam plant designated as 41-49 RZ, which have been deposited on Jan. 27, 2010, under the terms of the Budapest Treaty, with the National Collections of Industrial, Marine and Food Bacteria (NCIMB) in Bucksburn, Aberdeen AB21 9YA, Scotland, UK and have been assigned NCIMB Accession No. 41692. Deposited seed will be irrevocably and without restriction or condition released to the public during the effective term of any patent issued from this application As used herein, romaine may be *Lactuca sativa* L. var. longifolia Lam; also known as cos. The plant develops in an upright open or upright compact growing habit with coarse textured leafs. The younger leaves are longer than they are wide, fifteen cupping together to form an elongated loose head. Leaf margins are often entire or undulated, rarely frilled. Outer leaves range in color from light green to dark green. Inner heartleaves are smaller and range from light yellow to light green in color.

Figure 1:
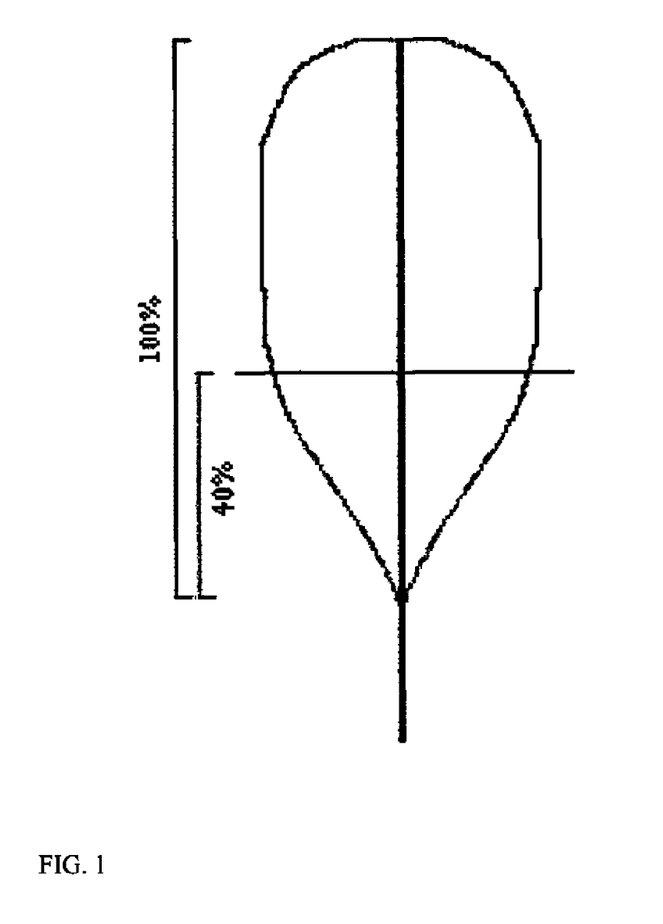
FIG. 1 shows a transverse section at 40% of leaf lamina length to observe solidness of main vein.

As used herein, a hollow main vein may be the main vein of a fully-grown tenth to fifteenth leaf, which is characterized by the fact that the vein is hollow, which is observed by visual inspection of a transverse section of the leaf. The transverse section should be made at 40% of the total leaf length, starting from the leaf base (see FIG. 1). For comparison two standard varieties can be used: Nirvanus, with hollow veins, and 41-53 RZ, with solid veins.

As used herein, a broad base leaf may be characterized by a length/width-ratio of 1.5 or lower. A mature romaine lettuce plant has got broad base leaves if the average length/width-ratio of the fully-grown tenth to the fifteenth leaf is 1.5 or lower. For comparison two standard varieties may be used: Nirvanus with broad base leaves (see, e.g., NCIMB Accession No. 41326 and U.S. Pat. No. 7,504,562, the disclosure of which is incorporated by reference), and 41-53 RZ with narrow base leaves (see, e.g., NCIMB Accession No. 41536 and U.S. patent application Ser. No. 12/321,249, the disclosure of which is incorporated by reference).

As used herein, resistance against *Bremia lactucae* Regal may be defined as the ability of a plant to resist infection by one or more various strains of *Bremia lactucae* (such as, but not limited to, NL1, NL2, NL4, NL5, NL6, NL7, NL10, NL12, NL13, NL14, NL15, NL16, B1:17, B1:18, B1:20, B1:21, B1:22, B1:23, B1:24, B1:25, B1:26, USA912, F535, CA-I, IIa, IIb, IV, V, VI, VII and VIII; Van Ettekoven K, Van der Arend A J M, 1999. In: Lebeda A, Kristkova E (eds.) Eucarpia leafy vegetables '99. Palacky University, Olomouc, Czech Republic, 1999: 171-175; Van der Arend et al., 2003. In: Van Hintum et al. (Eds.) Eucarpia Leafy Vegetables 2003. CGN, Wageningen, the Netherlands 2003: 151; Van der Arend et al., 2006. In: Pink et al. (Eds.) Eucarpia Leafy Vegetables 2006. Warwick HRI, Wellesbourne, UK, 2007; Michelmore and Ochoa, 2009. Crisphead lettuce breeding. In: California Leafy Vegetables Board, Annual Report 2008-2009 incorporated herein by reference; *Bremia* strains USA912 and F535 were isolated in California, USA and France, respectively, and are available from Rijk Zwaan) via a hypersensitivity response (Crute, I. R., Annual Rev. Phytopathol., 30:485-506, 1992; incorporated herein by reference).

Resistance may be defined as the capacity of the plant to resist infection by each of the various strains of *Bremia lactucae* Regal in all stages between the seedling stage and the harvestable plant stage. Resistance typically may be tested by two interchangeable methods, described by Bonnier, F. J. M. et al. (Euphytica, 61(3):203-211, 1992; incorporated herein by reference). One method involves inoculating 7-day old seedlings, and observing sporulation 10 to 14 days later. The other method involves inoculating leaf discs with a diameter of 18 mm obtained from a non-senescent, fully grown true leaf and observing sporulation 10 days later.

In the USA the *Bremia*-resistance gene Dm17 may be effective against the officially denominated CA-strains; (Maisonneuve et al., 1994. Rapid mapping of two genes for resistance to downy mildew from *lactuca serriola* to existing clusters of resistance genes. Theoretical and Applied Genetics 89: 96-104; Michelmore and Ochoa, 2009. Crisphead lettuce breeding. In: California Leafy Vegetables Board, Annual Report 2008-2009). Its presence may be tested by inoculation with a well-chosen *Bremia*-strain or by testing with DNA-markers closely linked to the gene.

As used herein, resistance against *Nasonovia ribisnigri* (Mosley), or currant-lettuce aphid, may be defined as the plant characteristic which results in a non-feeding response of the aphid on the leaves of the plant in all stages between 5 true-leaf stage and harvestable plant stage (U.S. Pat. No. 5,977,443 to Jansen, J. P. A., "Aphid Resistance in Composites," p. 12, 1999; incorporated herein by reference).

Resistance may be tested by spreading at least ten aphids on a plant in a plant stage between 5 true leaves and harvestable stage, and observing the density of the aphid population on the plant as well as the growth reduction after 14 days in a greenhouse, with temperature settings of 23 degrees Celsius in daytime and 21 degrees Celsius at night. Day length may be kept at 18 hours by assimilation lights.

As used herein, resistance against *Sphingomonas suberifaciens* (van Bruggen et al., International Journal of Systematic Bacteriology., 40: 2, 175-188 (1990) Yabuuchi et al., Microbiol. Immunol 43: 339-349 (1999), also known as corky root or *Rhizomonas suberifaciens*, may be the ability of the plant to grow relatively normally in a corky root infected soil. As the resistance is incomplete, a susceptible and a resistant standard variety, for example 'Parris Island' (susceptible) and 'Tall Guzmaine' (resistant), may be used for comparison. It may be tested by a young plant test in the greenhouse, as described by Brown & Michelmore Phytopathology 78: 1145-1150 (1988)) using the CA1-strain (van Bruggen et al., (International Journal of Systematic Bacteriology., 40: 2, 175-188 (1990)).

As used herein, resistance against lettuce mosaic virus (LMV) may be defined as the ability of the plant to grow normally after LMV infection and to inhibit the virus transmission via seed. Resistance may be tested by mechanical inoculation of young plants in a climate cell or a greenhouse, as described by Pink, D. A. C. et al. (Plant Pathology, 41(1): 5-12, 1992), incorporated herein by reference. Inoculated resistant plants grow just as well as uninoculated plants and show no chlorosis or mosaic symptoms. The LMV isolate, which may be used for testing, is Ls-1 (International Union for the Protection of New Varieties of Plants [UPOV], Guidelines for the conduct of tests for distinctness, uniformity and stability; lettuce (*Lactuca sativa* L.), 2002, p. 35; incorporated herein by reference).

As used herein, dark green outer leaves may be defined by the color of a fully-grown tenth to fifteenth leaf, which should be similar to or darker than 137B, 138A, 144A, or 146A on the RHS color chart (The Royal Horticultural Society, London, UK).

In an embodiment of the present invention, there is provided a lettuce plant or parts thereof produced by growing the seed of lettuce cultivar 41-49 RZ.

The lettuce of the present invention may be a romaine lettuce (*Lactuca sativa* L. var. longifolia Lam) plant. The leaves may have a hollow main vein, broad base leaves or resistance to downy mildew (*Bremia lactucae* Regal), currant-lettuce aphid (*Nasonovia ribisnigri*), corky root (*Sphingomonas suberifaciens*) and lettuce mosaic virus (LMV) or any combination thereof.

The lettuce of the present invention may be suitable for harvesting hearts and wholeheads.

The lettuce of the present invention may be resistant to *Nasonovia ribisnigri* (currant-lettuce aphid); *Nasonovia ribisnigri* (currant-lettuce aphid); *Bremia lactucae* races CA-VII,VIII; *Bremia lactucae* races B1:4,6,10,12,13,14,15,21; *Bremia lactucae* races B1:16,23; *Bremia lactucae* races B1:17,18,20,22,24,25,26; LMV; corky root (*Sphingomonas suberifaciens*) or any combination thereof.

In another embodiment, there is provided pollen, ovules, and tissue cultures of regenerable cells from the plant produced by growing the seed of lettuce cultivar 41-49 RZ, in which the cells or protoplasts of the tissue that are cultured are produced from a tissue selected from leaves, pollen, embryos, cotyledon, hypocotyls, meristematic cells, roots, root tips, anthers, flowers, seeds or stems.

In still another embodiment, there is provided a transgenic version of the lettuce cultivar 41-49 RZ and seed thereof. Numerous methods for plant transformation have been developed, including biological and physical, plant transformation protocols. See, for example, Miki et al., "Procedures for Introducing Foreign DNA into Plants" in Methods in Plant Molecular Biology and Biotechnology, Glick B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in Methods in Plant Molecular Biology and Biotechnology, Glick B. R. and Thompson, J. E. Eds. (CRC Press, Inc., Boca Raton, 1993) pages 89-119.

In a further embodiment, there is provided a lettuce plant regenerated from the above-described tissue cultures, in which the regenerated plant has all of the morphological and physiological characteristics of lettuce cultivar 41-49 RZ.

In still a further embodiment, a method is provided for producing a hybrid lettuce seed comprising crossing a first parent lettuce plant with a second parent lettuce plant and harvesting the resultant hybrid lettuce seed, wherein the first parent lettuce plant or the second parent lettuce plant is the lettuce plant produced by growing the seed of lettuce cultivar 41-49 RZ.

In still another embodiment, a method is provided for developing a lettuce cultivar suitable for harvesting as hearts and wholeheads comprising crossing a mother lettuce plant cultivar with a father lettuce plant cultivar to produce a hybrid seed; growing the hybrid seed to produce a hybrid plant; selfing the hybrid seed to produce F2 progeny seed; and selecting the F2 plants for having well-shaped hearts.

In a preferred embodiment, the specific type of breeding method employed for developing a lettuce cultivar is pedigree selection, where both single plant selection and mass selection practices are employed. Pedigree selection, also known as the "Vilmorin system of selection," is described in Fehr, W., Principles of Cultivar Development, Volume I, MacMillan Publishing Co., which is hereby incorporated by reference.

When pedigree selection is applied, in general selection is first practiced among F2 plants. In the next season, the most desirable F3 lines are first identified, and then desirable F3 plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce F1 offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype can be used in the method of the present invention.

The F1 may be self-pollinated to produce a segregating F2 generation. Individual plants may then be selected which represent the desired phenotype in each generation (F3, F4, F5, etc.) until the traits are homozygous or fixed within a breeding population.

The present invention is more particularly described in the following non-limiting example, which is intended to be illustrative only, as numerous modifications and variations therein will be apparent to those skilled in the art.

EXAMPLE 1

Development and Characteristics of Lettuce Cultivar 41-49 RZ

The breeding history of the 41-49 RZ started in Aramon, France in 2003 with a cross between a plant of the romaine breeding line '03A.52746' as mother and a plant from the romaine breeding line '03A.54819' as father with the aim to combine a good heart quality with extensive *Bremia*-resistance.

The F1 designated '04A.98137' was sown in the spring 2004 to produce F2-seed in a greenhouse in Aramon. The F2-seed, designated '05A.50406', was sown in a spring trial in Tarascon, France in 2005. In April 2005 an F2-plant was selected from the trial for being a dark green, *Nasonovia*-, *Bremia*-, corky root- and LMV-resistant romaine type with a good head shape. The F2-plant produced F3-seed, designated '06A.50696', which was sown in an early summer trial in Daylesford, Australia in October 2005.

In January 2006 an F3-plant was selected from the trial for being a dark green, *Nasonovia*-, *Bremia*-, corky root- and LMV-resistant romaine type with a good head shape. The F3-plant produced F4-seed, designated '07A.50217', which was sown in a summer trial in Aramon, France in 2006. In September 2006 an F4-plant was selected from the trial for being a dark green, *Nasonovia*-, *Bremia*-, and LMV-resistant romaine type with good head shape. The F4-plant produced F5-seed, designated 07A.52936, which was sown in a spring trial in Tarascon, France in 2007.

In April 2007 an F5-plant was selected from the trial for being a dark green, *Nasonovia*-, *Bremia*-, corky root- and LMV-resistant romaine type with a good head shape. The F5-plant produced F6-seed, designated '08A.51890', which was sown in a summer trial in Aramon, France in 2007. In September 2007 an F6-plant was selected from the trial for being a dark green, *Nasonovia*-, *Bremia*-, and LMV-resistant romaine type with good head shape. The F6-plant produced F7-seed, designated 08A.52585, which was uniform for type, field performance, disease-resistance, bolting, colour, and head shape (all based on several trials in 2008).

The F7-seed was used to sow a multiplication in Aramon, France in April 2008. The plants showed phenotypical uniformity during seed production and seed was harvested for further trialing in 2009 on confidential sites. The seed lot was designated by the introduction number '41-49 RZ'.

In Table 1 that follows, the traits and characteristics of the *Lactuca sativa* L. var. longifolia Lam romaine lettuce plant having the designation 41-53 RZ, are given compared to the mentioned comparison varieties, referred to as "41-53 RZ", "Nirvanus", " ", and "Helvius".

TABLE 1

| Character | "41-49 RZ" | "41-53 RZ" | "Nirvanus" | "Helvius" |
|---|---|---|---|---|
| Type | romaine or cos | romaine or cos | romaine or cos | romaine or cos |
| Hollow/solid main vein | Hollow | Solid | Hollow | Hollow |
| Broad/narrow base leaves | Broad | Broad | Broad | Broad |
| Blond/dark green color | Dark | Dark | Dark | Dark |

| trait | Salvius | 41-53 RZ | Nirvanus | Helvius |
|---|---|---|---|---|
| resistance to *Bremia lactucae* races CA-VII, VIII | present | present | absent | present |
| resistance to *Bremia lactucae* races B1: 16, 23 | present | absent | present | present |
| resistance to *Bremia lactucae* races B1: 17, 18, 20, 22, 24, 25, 26 | present | present | absent | present |
| resistance to *Bremia lactucae* races USA912 and F535 | present | present | absent | absent |
| *Bremia*-resistance gene Dm17 | present | present | absent | absent |
| resistance to corky root (*Sphingomonas suberifaciens*) | present | absent | present | present |

In the Tables that follow, the traits and characteristics of the *Lactuca sativa* L. var. longifolia Lam romaine lettuce plant referred to as "41-49 RZ" are given compared to the most similar variety, referred to as "Helvius" and a standard regional check variety, referred to as "Parris Island." Observations were made in a trial in Wageningen, the Netherlands in 2007. Sowing date was 27 March; transplanting date was 24 April.

In Table 2, the seed color, cotyledon shape and characteristics of the fourth leaf of "41-53 RZ" is compared with "Actarus" and "Parris Island." RHS=Royal Horticulural Society colour chart code.

TABLE 2

Figure 2:
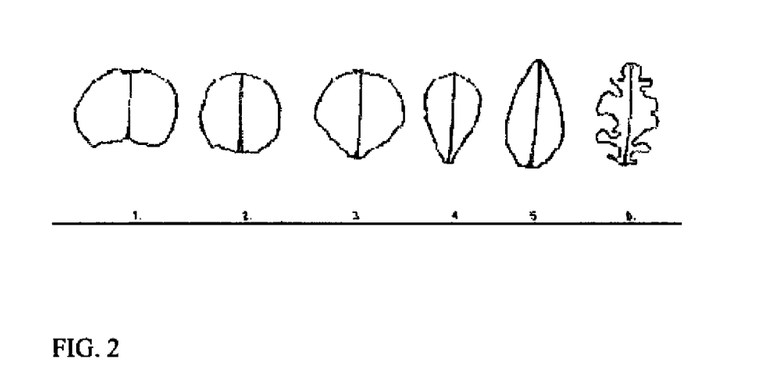
FIG. 2 shows possible shapes of cotyledon of fourth leaf.
Figure 3:
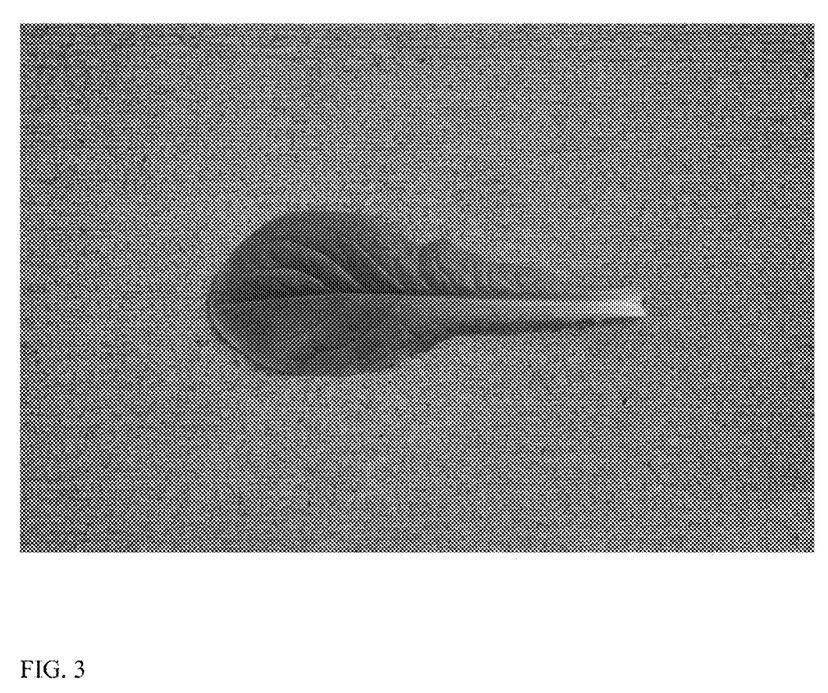
FIG. 3 shows a fourth leaf of 41-49 RZ.
Figure 4:
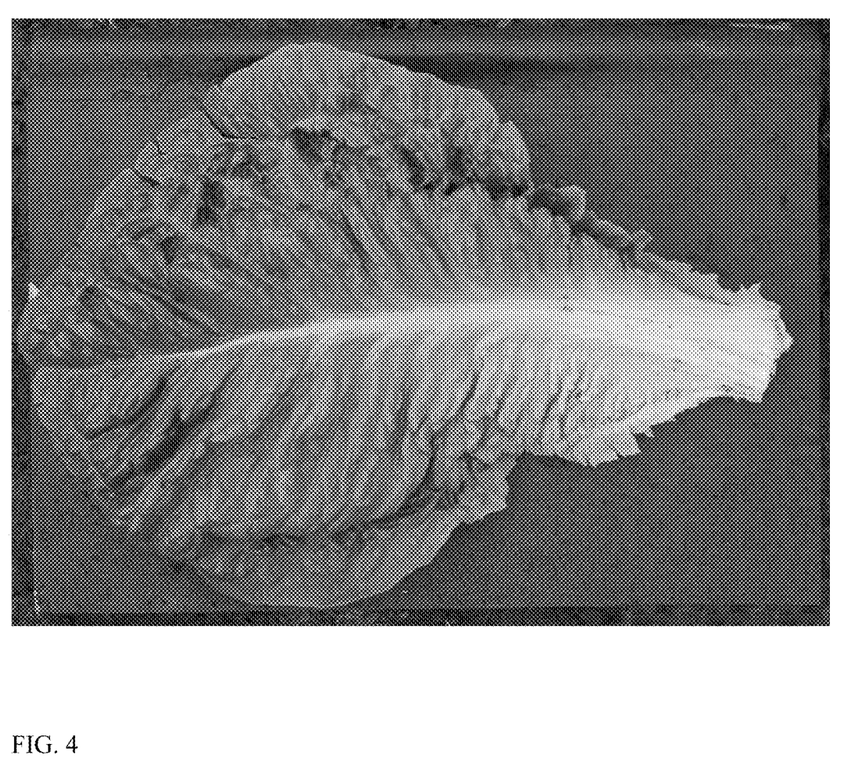
FIG. 4 shows a mature leaf of 41-49 RZ.

| Character | "41-49 RZ" | "Helvius" | "Parris Island" |
|---|---|---|---|
| Plant Type | Romaine or Cos | Romaine or Cos | Romaine or Cos |
| Seed Color | White (Silver Gray) | White (Silver Gray) | White (Silver Gray) |
| Cotyledon Shape | Intermediate | Intermediate | Spatulate |
| Cotyledon Shape of Fourth Leaf | No. 4 on FIG. 2 | No. 4 on FIG. 2 | No. 4 on FIG. 2 |

TABLE 2-continued

| Character | "41-49 RZ" | "Helvius" | "Parris Island" |
|---|---|---|---|
| Cotyledon Rolling of Fourth Leaf Stage | Very slightly | Present | slightly |
| Cotyledon Cupping of Fourth Leaf Stage | Uncupped | Uncupped | Uncupped |
| Fourth Leaf Apical Margin | Entire | Entire | Entire |
| Fourth Leaf Basal Margin | Coarsely Dentate | Coarsely Dentate | Coarsely Dentate |
| Undulation | Flat | Flat | Flat |

In Table 3, the mature leaf and head characteristics of "41-49 RZ" is compared with "Helvius" and "Parris Island."

TABLE 3

| Character | "41-49 RZ" | "Helvius" | "Parris Island" |
|---|---|---|---|
| Maturity (Earliness of Harvest-Mature Head Formation (Spring season) | 10576 days | 100 days | 100 days |
| Green Color | RHS 144A | RHS 144B | RHS 137A |
| Anthocyanin Distribution | Absent | Absent | Absent |
| Margin Incision Depth | Absent/Shallow | Absent/Shallow | Absent/Shallow |
| Margin Indentation | Entire | Entire | Entire |
| Undulations of the Apical Margin | Absent/Slight | Absent/Slight | Absent/Slight |
| Leaf Size | Large | Large | Large |
| Leaf Glossiness | Glossy | Moderate | Moderate |
| Leaf Blistering | Strong | Moderate | Moderate |
| Leaf Thickness | Thick | Thick | Thick |
| Trichomes | Absent (Smooth) | Absent (Smooth) | Absent (smooth) |
| Spread of Frame Leaves | 40 cm | 40 cm | 39 cm |
| Head Diameter | 10 cm | 8 cm | 9 cm |
| Head Shape | Elongate | Elongate | Elongate |
| Head Size | Large | Large | Large |
| Head Weight | 610 g | 579 g | 504 g |
| Head Firmness | Firm | Firm | Firm |
| Butt Shape | Rounded | Rounded | Rounded |
| Midrib | Prominently Raised | Prominently Raised | Prominently Raised |

In Table 4, the characteristics of the core and the bolter plant of "41-49 RZ" is compared with "Helvius" and "Parris Island."

TABLE 4

| Character | "41-53 RZ" | "Actarus" | "Parris Island" |
|---|---|---|---|
| Core Diameter at Base of Head | 38 mm | 39 mm | 42 mm |
| Ratio of Head Diameter/Core Diameter | 2.7 | 2.1 | 2.1 |
| Core Height from Base of Head to Apex | 69 mm | 64 mm | 54 mm |
| Number of Days from first water date to seed stalk emergence | 123 | 123 | 126 |
| Bolting Class | Slow | Slow | Slow |
| Height of Mature Seed Stalk | 100 cm | 120 cm | 90 cm |
| Spread of Bolter Plant | 30 cm | 30 cm | 30 cm |
| Bolter Leaves | Straight | Straight | Straight |
| Margin | Dentate | Dentate | Dentate |
| Terminal Inflorescence | Absent | Absent | Absent |
| Lateral Shoots | Present | Present | Present |
| Basal Side Shoots | Present | Present | Present |

While the invention has been particularly shown and described with reference to preferred embodiments thereof, it will be understood by those skilled in the art that various alterations in form and detail may be made therein without departing from the spirit and scope of the invention.

What is claimed is:

1. A lettuce plant of the cultivar designated 41-49 RZ, representative seed of which having been deposited under NCIMB Accession No. 41692, wherein said plant is a romaine lettuce (*Lactuca sativa* L. var. longifolia Lam) plant, and has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV).

2. A seed of the plant of claim 1.

3. A lettuce plant that has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) of lettuce plant of cultivar 41-49 RZ, representative seed of which having been deposited under NCIMB Accession No. 41692 and is grown from seeds as described in claim 2.

4. A $F_1$, $F_2$, $F_3$, $F_4$, $F_5$, $F_6$, or $F_7$ progeny of a lettuce plant of claim 3, wherein the progeny has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) of lettuce plant of cultivar 41-49 RZ, representative seed of which having been deposited under NCIMB Accession No. 41692.

5. A part of the plant of claim 1 that is suitable for sexual reproduction.

6. The part as described in claim 5, selected from the group consisting of microspores, pollen, ovaries, ovules, embryo sacs, and egg cells.

7. A lettuce plant that has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) of lettuce plant of cultivar 41-49 RZ, representative seed of which having been deposited under NCIMB Accession No. 41692 and is regenerated from parts as described in claim 3.

8. A $F_1$, $F_2$, $F_3$, $F_4$, $F_5$, $F_6$, or $F_7$ progeny of a lettuce plant of claim 7, wherein the progeny has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) of lettuce plant of cultivar 41-49 RZ, representative seed of which having been deposited under NCIMB Accession No. 41692.

9. A part of the plant of claim 1 that is suitable for vegetative reproduction.

10. The part as described in claim 9 selected from the group consisting of cuttings, roots, stems, cells, and protoplasts.

11. A tissue culture of a lettuce plant of claim 1.

12. The tissue culture as described in claim 11, which is derived from the group consisting of leaves, pollen, embryos, cotyledon, hypocotyls, meristematic cells, roots, root tips, anthers, flowers, seeds and stems.

13. A lettuce plant that has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) of lettuce plant of cultivar 41-49 RZ, representative seed of which having been deposited under NCIMB Accession No. 41692 and is regenerated from a tissue culture as described in claim 11.

14. A $F_1$, $F_2$, $F_3$, $F_4$, $F_5$, $F_6$, or $F_7$ progeny of a lettuce plant of claim 13, wherein the progeny has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) of lettuce plant of cultivar 41-49 RZ, representative seed of which having been deposited under NCIMB Accession No. 41692.

15. A $F_1$, $F_2$, $F_3$, $F_4$, $F_5$, $F_6$, or $F_7$ progeny of a lettuce plant of claim 1, wherein the progeny has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) of lettuce plant of cultivar 41-49 RZ, representative seed of which having been deposited under NCIMB Accession No. 41692.

16. A $F_1$, $F_2$, $F_3$, $F_4$, $F_5$, $F_6$, or $F_7$ progeny of a lettuce plant of claim 1, wherein said plant is a romaine lettuce (*Lactuca sativa* L. var. longifolia Lam) plant, and has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) as found in lettuce cultivar 41-49 RZ, representative seed of which having been deposited under NCIMB Accession No. 41692, and is modified in one or more other characteristics.

17. The progeny as described in claim 16, wherein the modification is effected by transformation with a transgene.

18. A $F_1$ progeny of a lettuce plant, which is produced by sexual reproduction of a lettuce plant of claim 1, wherein the regenerated plant has leaves with a hollow main vein, broad base leaves and resistance to downy mildew (*bremia Lactucae* Regal), currant-lettuce aphid (*Nasonovia ribisnigri*), corky root (*Sphingomonas suberifaciens*) and lettuce mosaic virus (LMV) of lettuce plant cultivar 41-49 RZ, representative seed of which having been deposited under NCIMB Accession No. 41692.

19. A $F_2$, $F_3$, $F_4$, $F_5$, $F_6$, or $F_7$ progeny of a lettuce plant, which is produced by sexual reproduction of a progeny plant of a lettuce plant of claim 1, wherein the regenerated plant has leaves with a hollow main vein, broad base leaves and resistance to downy mildew (*bremia Lactucae* Regal), currant-lettuce aphid (*Nasonovia ribisnigri*), corky root (*Sphingomonas suberifaciens*) and lettuce mosaic virus (LMV) of lettuce plant cultivar 41-49 RZ, representative seed of which having been deposited under NCIMB Accession No. 41692.

20. A progeny of a lettuce plant which is produced by vegetative reproduction of a lettuce plant of claim 1 or a progeny plant thereof, wherein the regenerated plant has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) of lettuce plant cultivar 41-49 RZ, representative seed of which having been deposited under NCIMB Accession No. 41692.

21. A lettuce plant that has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) of lettuce plant of cultivar 41-49 RZ, representative seed of which having been deposited under NCIMB Accession No. 41692.

22. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of claim 1 or 21.

23. A method of producing a lettuce plant that has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) of lettuce plant of cultivar 41-49 RZ, representative seed of which having been deposited under NCIMB Accession No. 41692 comprising crossing a first lettuce plant with a second lettuce plant wherein the first or second lettuce plant is the lettuce plant of claim 1 or 21.

24. A lettuce plant which has leaves with a hollow main vein, broad base leaves and resistance to downy mildew (*Bremia lactucae* Regal), currant-lettuce aphid (*Nasonovia ribisnigri*), corky root (*Sphingomonas suberifaciens*) and lettuce mosaic virus (LMV) of lettuce plant of cultivar 41-49 RZ, representative seed of which having been deposited under NCIMB Accession No. 41692 wherein the plant is produced by the method of claim 23.

25. The lettuce plant of claim 1 or 21 generated from seed deposited under NCIMB Accession No. 41692.

26. A method of producing a lettuce cultivar being a romaine lettuce (*Lactuca sativa* L. var. longifolia Lam) plant, and having leaves with a hollow main vein, broad base leaves, resistance to downy mildew (*Bremia lactucae* Regal), currant-lettuce aphid (*Nasonovia ribisnigri*), corky root (*Sphingomonas suberifaciens*) and lettuce mosaic virus (LMV), comprising: (a) crossing a mother lettuce plant with a father lettuce plant to produce a hybrid seed; (b) growing said hybrid seed to produce a hybrid plant; (c) selfing said hybrid seed to produce $F_2$ progeny seed; and (d) selecting said $F_2$ plants for being a romaine lettuce (*Lactuca sativa* L. var. longifolia Lam) plant and having leaves with a hollow main vein, broad base leaves, and resistance to downy mildew (*Bremia lactucae* Regal), corky root (*Sphingomonas suberifaciens*), currant-lettuce aphid and lettuce mosaic virus (LMV).

\* \* \* \* \*